US007908293B2

(12) United States Patent
Aronson et al.

(10) Patent No.: US 7,908,293 B2
(45) Date of Patent: Mar. 15, 2011

(54) MEDICAL LABORATORY REPORT MESSAGE GATEWAY

(75) Inventors: Samuel J. Aronson, Brookline, MA (US); Lawrence J. Babb, North Grafton, MA (US); Mollie Ullman-Cullere, Newtonville, MA (US); Eugene H. Clark, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 318 days.

(21) Appl. No.: 12/031,492

(22) Filed: Feb. 14, 2008

(65) Prior Publication Data

US 2008/0270438 A1 Oct. 30, 2008

Related U.S. Application Data

(60) Provisional application No. 60/889,788, filed on Feb. 14, 2007.

(51) Int. Cl.
*G06F 17/00* (2006.01)
(52) U.S. Cl. ......... 707/791; 707/802; 707/822; 707/828
(58) Field of Classification Search ........... 707/600–831
See application file for complete search history.

(56) References Cited

U.S. PATENT DOCUMENTS

| | | | |
|---|---|---|---|
| 5,890,129 A | 3/1999 | Spurgeon | |
| 2001/0016822 A1* | 8/2001 | Bessette | 705/3 |
| 2004/0064343 A1 | 4/2004 | Korpman et al. | |

OTHER PUBLICATIONS

HealthShare product web page, InterSystems Corporation, Feb. 8, 2007.
The Requirements of Health Information Exchanges—and How HealthShare Satisfies Them, InterSystems Corporation, Jan. 29, 2007.
Creating Health information Exchanges With InterSystems HealthShare, InterSystems Corp., 2006.
Ensemble HL7v2 Development Guide, Version 4.0, InterSystems Corporation, Jul. 27, 2006.
Ensemble HL7v2 Technical Reference, Version 4.0, InterSystems Corporation, Jul. 27, 2006.
Ensemble HL7v2 User Interface Guide, Version 4.0, InterSystems Corporation, Jul. 27, 2006.
Ensemble HL7v3 Development Guide, Version 4.0, InterSystems Corporation, Jul. 27, 2006.
Introducing Ensemble, Version 4.0, InterSystems Corporation, Jul. 27, 2006.
Ensemble Data Transformation Language Reference, Version 4.0, InterSystems Corporation, Jul. 27, 2006.
Using File Adapters with Ensemble, Version 4.0, InterSystems Corporation, Jul. 27, 2006.

(Continued)

*Primary Examiner* — Isaac M Woo
(74) *Attorney, Agent, or Firm* — Quarles & Brady LLP

(57) ABSTRACT

A medical laboratory report communications gateway computer system is presented. The gateway is configured to receive medical laboratory reports from a plurality of clients. The gateway uses report form data stored in a database to perform an inbound translation on the medical laboratory report to transform the medical laboratory report to a canonical form. The gateway identifies a destination client for the medical laboratory report, and determines an outbound message form based on the destination client. The gateway performs the selected outbound translation on the medical laboratory report in the canonical form to transform the medical laboratory report in the canonical form into a form useable by the destination client. The gateway then transmits the translated medical laboratory report to the destination client.

15 Claims, 8 Drawing Sheets

OTHER PUBLICATIONS

Using Workflow with Ensemble, Version 4.0, InterSystems Corporation, Jul. 27, 2006.
Developing Ensemble Productions, Version 4.0, InterSystems Corporation, Jul. 27, 2006.
"GIGPAD, Infrastructure to Support Genetic, Genomic and Proteomic Assays", Sandy Aronson, Harvard Medical School, 2006.
"Harvard's Personalized Medicine Gateway," Steven Withrow, Bio-IT World, Aug. 15, 2005.
Improving Health and Accelerating Personalized Health Care through Health Information Technology, Harvard Medical School, Jan. 10, 2007.
Rhapsody Integration Engine Technical Details, Orchestral Developments Limited, 2006.
Rhapsody Integration Engine Product Overview, Orchestral Developments Limited, 2006.
Sun SeeBeyond, Java Composite Applications Platform Suite Primer, Release 5.1.0, Sun Microsystems, 2006.
MD Link Integration, MDI Solutions Limited, Feb. 1, 2005.
NeoIntegrate Features Overview, NeoTool, LLC, Feb. 2007.
"The seventh layer of the clinical-genomics information infrastructure", A. Shabo, et al., IBM Systems Journal, vol. 46, No. 1, 2007.
Donor Management System (DMS) product information web page, 5d Information Management, 2, 2006.
"Respectful Type Converters," Jeannette M. Wing, et al., IEEE Transactions on Software Engineering, vol. 26, No. 7, Jul. 2000.
HL7 Introduction, Jan. 12, 2008 (http://nule.org/wp/?page_id=99).
HL7 to Application Tutorial, Part I, Sep. 18, 2007 (http://www.interfaceware.com/manual/Chameleon_Tutorial_Parsing_HL7.html).
HL7 to Application Tutorial, Part II, Sep. 18, 2007 (http://www.interfaceware.com/manual/Chameleon_Tutorial_Parsing_HL7.html).
HL7 to Application Tutorial, Part III, Sep. 18, 2007 (http://www.interfaceware.com/manual/Chameleon_Tutorial_Parsing_HL7.html).
HL7 to Application Tutorial, Part IV, Sep. 18, 2007 (http://www.interfaceware.com/manual/Chameleon_Tutorial_Parsing_HL7.html).
HL7 to Application Tutorial, Part V, Sep. 18, 2007 (http://www.interfaceware.com/manual/Chameleon_Tutorial_Parsing_HL7.html).
HL7 to Application Tutorial, Part VI, Sep. 18, 2007 (http://www.interfaceware.com/manual/Chameleon_Tutorial_Parsing_HL7.html).
HL7 to Application Tutorial, Part VII, Sep. 18, 2007 (http://www.interfaceware.com/manual/Chameleon_Tutorial_Parsing_HL7.html).
HL7 to Application Tutorial, Part VIII, Sep. 18, 2007 (http://www.interfaceware.com/manual/Chameleon_Tutorial_Parsing_HL7.html).
HL7 to Application Tutorial, Part IX, Sep. 18, 2007 (http://www.interfaceware.com/manual/Chameleon_Tutorial_Parsing_HL7.html).
HL7 to Application Tutorial, Part X, Sep. 18, 2007 (http://www.interfaceware.com/manual/Chameleon_Tutorial_Parsing_HL7.html).
HL7 to Application Tutorial, Part XI, Sep. 18, 2007 (http://www.interfaceware.com/manual/Chameleon_Tutorial_Parsing_HL7.html).
HL7 to Application Tutorial, Part XII, Sep. 18, 2007 (http://www.interfaceware.com/manual/Chameleon_Tutorial_Parsing_HL7.html).
HL7 to Application Tutorial, Part XIII, Sep. 18, 2007 (http://www.interfaceware.com/manual/Chameleon_Tutorial_Parsing_HL7.html).
HL7 to Application Tutorial, Part XIV, Sep. 18, 2007 (http://www.interfaceware.com/manual/Chameleon_Tutorial_Parsing_HL7.html).
HL7 to Application Tutorial, Part XV, Sep. 18, 2007 (http://www.interfaceware.com/manual/Chameleon_Tutorial_Parsing_HL7.html).
HL7 to Application Tutorial, Part XVI, Sep. 18, 2007 (http://www.interfaceware.com/manual/Chameleon_Tutorial_Parsing_HL7.html).
HL7 to Application Tutorial, Part XVII, Sep. 18, 2007 (http://www.interfaceware.com/manual/Chameleon_Tutorial_Parsing_HL7.html).
HL7 to Application Tutorial, Part XVIII, Sep. 18, 2007 (http://www.interfaceware.com/manual/Chameleon_Tutorial_Parsing_HL7.html).
HL7 to Application Tutorial, Part XIX, Sep. 18, 2007 (http://www.interfaceware.com/manual/Chameleon_Tutorial_Parsing_HL7.html).
HL7 to Application Tutorial, Part XX, Sep. 18, 2007 (http://www.interfaceware.com/manual/Chameleon_Tutorial_Parsing_HL7.html).
Partial Search Report from PCT/US2008/054008, Jan. 7, 2008.
The International Search Report and the Written Opinion of the International Searching Authority, International Application No. PCT/US2008/054008, International Searching Authority, Oct. 21, 2008, 77 pages.

* cited by examiner 404 406                                              400
            \   \                                               /
         MSH|^~\&|PP|LMM|VWG|MHC| ||ORU^R01| |T|2.3     424

408 ——  PID| |61527|0000004^^^1|BABB^LAWRENCE^J^JR|...

410 ——  PV1|1|||||^^^^^^^^|A03609^HYMAN^BRADLEY^T^^^M.D.^^...

414 ——  ORC|SC||PM06J00705^AP||L|||200608081416|MV||...

418 ——  OBR|1|04900260|PM06J00705|SURG^Blood,Peripheral...

Z01|103538956||06222244||9999999|0000004...

Z04|XML String|

<?xml version="1.0" encoding="UTF-8"?>

<geneticTestOrder xmlns="http://www.partners.org/genetics" ...

<status>Complete</status>

<order><indicationCode text="Family History"/><testCategoryCode code="Diagnostic"/>

<overallResult>Positive</overallResult>

<resultDisplay>

<resultItem><displayLine>1468G\T\gt;A (G490R), Exon 17, ...

<resultItem><displayLine>3697C\T\gt;T (Q1233X), Exon 33, ...

</resultDisplay>

<variants count="3">

<sequenceVariant><dnaChange level="Intragenic" type="Substitution">

...

</geneticTestOrder>

420 ——  OBX|1|FT|REPORT|1|CASE: PM-06-J00705|||||F|||200608081416

OBX|2|FT|REPORT|2|PATIENT: SANTA CLAUS|||||F|||200608081416

428 ——  OBX|3| ... GENE ACTC1 ^HGNC ...
                    /     /       \
                  430    438       434

<Patient>

<Last>Babb</Last>

<First>Lawrence</First>

<MI>J</MI>

</Patient>

.

.

.

<DN Variant>C.512C > G</DNA Variant>

FIG. 5

MEDICAL LABORATORY REPORT MESSAGE GATEWAY

The present application claims priority from U.S. Provisional Patent Application No. 60/889,788, filed Feb. 14, 2007, which is incorporated herein by reference.

TECHNICAL FIELD

The present invention relates to message gateways and, more particularly, to message gateways for receiving, translating and sending medical laboratory report messages.

BACKGROUND ART

Health care providers ("providers"), including hospitals, clinics and doctor's offices, routinely order laboratory tests for patients. These tests include blood analyses, pathological analyses, radiological analyses and, more recently, genetic and genomic analyses. The tests are performed by third-party laboratories, many of which specialize in the types of analyses they perform. Laboratories that provide genetic or genomic analysis are particularly likely to perform highly specialized, and sometimes proprietary, analyses. Thus, a provider may use many laboratories, particularly genetic or genomic laboratories, to meet all its analytical needs, and a laboratory, particularly a genetic or genomic laboratory, may perform analyses for many different providers.

Orders for these tests are often sent on paper, typically via facsimile transmission ("fax") from the providers to the laboratories. The laboratories then perform the tests and send results back to the providers, typically also via fax. The results may include reports, which are typically narratives, and/or results, which are typically data. In some cases, a test and interpretation of test results are performed by different organizations. For simplicity, the term "laboratory" is used herein to mean an organization that performs tests and/or analyzes or interprets test results.

Some providers maintain electronic medical records (EMRs), which contain patient data. However, laboratory analyses received in paper form are not easily added to an EMR. Adding information from paper-based analyses to an EMR is costly and error-prone.

Some laboratories are equipped to receive orders electronically directly from providers, and some laboratories are equipped to send analyses electronically directly to providers. Similarly, some providers are equipped to send orders and receive analyses electronically to and from laboratories. However, even many electronic messages are not sufficiently structured to facilitate automatically adding message information to an EMR in a manner that makes the information useful for clinical support.

Furthermore, a variety of message syntaxes and schemas are used by providers and laboratories to convey orders and analyses. Collectively, syntax and schema determine two parts of a message "form," as discussed in detail below. Each provider and each laboratory may use a different message form. Sometimes the message form further depends on an application or device (collectively hereinafter "application") used by a provider to request an analysis or on an application used by a laboratory to perform a requested analysis. Although many providers and laboratories use standards-based message protocols, such as Health Level Seven (HL7), differences exist among the message forms, even among organizations that use a given protocol, due to differences in how these organizations interpret the protocol, differences among various versions of a given protocol, individual organizations' data needs, how the providers structure their respective EMR systems, etc.

In addition to syntactic and schematic differences, other details of a message's form often depend on the sender of the message. For example, analyses often contain diagnostic codes. While many of these codes are standardized, others are not. In the rapidly expanding genetics or genomics sphere, codes for newly-discovered genetic variations are created, and the meanings of existing codes are changed, at a rapid rate. These additions and changes are not always made in a standardized manner or universally adopted. Thus, messages from a variety of laboratories are likely to be generated using a variety of proprietary vocabularies, leading to semantic differences among laboratories and between laboratories and providers.

The syntactic, schematic and semantic differences among laboratories and providers impede establishing electronic communications capabilities between the laboratories and the providers. To establish an electronic messaging capability between a provider and a laboratory, the parties must negotiate a form for messages each party sends to the other party. Often, the forms used between a provider and a laboratory are asymmetric, i.e., the provider sends messages in one form, and the laboratory sends messages in a different form. In many cases, the provider, the laboratory or both parties must modify their systems to accommodate the form used to send messages to, and receive messages from, the other party. Consequently, a custom built software interface is often required for one or both parties that wish to communicate electronically with each other.

Although some laboratories and some providers have developed some of these interfaces, each interface is expensive and time-consuming to construct and maintain. The cost to establish even a fraction of the number of interfaces a laboratory or provider would need to electronically communicate with all its peers is beyond the reach of most laboratories and providers.

Furthermore, not all applications are capable of sending or receiving a full set of electronic message types. For example, some versions of HL7 define four message types that, collectively, provide a "hand-shake" sequence. A "Results Complete" message is sent by a laboratory with a completed analysis. A provider may respond with a "Results Confirm Response" message to acknowledge receiving a Results Complete message. Alternatively, the provider may respond with a "Results Rejected Response" message. For example, this Results Rejected Response message may be sent if the Results Complete message from the laboratory is in an unacceptable form. In addition, after having sent a Results Complete message, a laboratory may send a "Results Corrected" message with updated or corrected analyses. Not all applications are capable of sending some or all of these messages. Thus, automated equipment in one party's location (such as in a laboratory) may not be fully taken advantage of by less capable equipment in the other party's location.

Thus, limitations exist in the abilities of laboratories and providers to electronically communicate orders and laboratory results, because not all laboratories and providers are equipped to communicate electronically, and even many of those that are so equipped would require prohibitively expensive interfaces to accommodate syntactic, schematic and semantic differences in messages from or to all their peers. In addition, the pace and volume of new discoveries in genetics and genomics is increasing the number of these differences and the complexity of creating and maintaining messaging interfaces.

SUMMARY OF THE INVENTION

An embodiment of the present invention provides a method for processing a medical laboratory test message. The method includes receiving the medical laboratory test message in a first form. The message includes a source identifier and has a message type. A first transformation is selected, based on the source identifier. A representation of the received message is generated in a second form, according to the first transformation. A second transformation is selected, based on the destination identifier. A second medical laboratory test message is generated in a third form, according to the second transformation. The second message is sent to a recipient, according to the destination identifier.

Receiving the medical laboratory test message may include receiving the message from one of a plurality of laboratories. Sending the second medical laboratory test message may include sending the second medical laboratory test message to a specific one of a plurality of medical service providers.

Generating the representation of the received message in the second form may include performing a first syntactic translation of the received message, according to the first transformation; performing a first schematic translation of the received message, according to the first transformation; and performing a first semantic translation of the received message, according to the first transformation.

Generating the second medical laboratory report message in the third form may include performing a second syntactic translation of the representation of the received message, according to the second transformation; performing a second schematic translation of the representation of the received message, according to the second transformation; and performing a second semantic translation of the representation of the received message, according to the second transformation.

The message may further include a message type. Sending the second message may include sending the second message to a recipient according to the message type.

The method may further include validating the contents of at least a portion of the received message, such as by validating a genetic code in at least a portion of the received message. The method may further include validating the contents of at least a portion of the representation of the received message, such as by validating a genetic code in at least a portion of the representation.

The method may further include selecting a plurality of recipients, based on the contents of the destination identifier. Selecting the second transformation may include, for each selected recipient, selecting a transformation associated with the selected recipient, based on the contents of the destination identifier. Generating the second medical laboratory report message may include, for each selected recipient, generating a medical laboratory report message, according to the transformation associated with the selected recipient. Sending the second message may include, for each selected recipient, sending the generated message to the selected recipient.

The source identifier may include a sending application identification, and the destination identifier may include a receiving facility identification.

The second form conforms to a clinical and administrative data message protocol, such as Health Level Seven (HL7), version three.

The medical laboratory report message may include genetic data or genomic data (collectively herein referred to as "genetic data").

The method may further include storing copies of at least some of the representations of the received messages in the second form and providing interactive access to the stored copies of the at least some of the representations of the received messages via a portal.

Another embodiment of the present invention provides a medical laboratory message gateway. The gateway includes a database storing translation information for each of a plurality of clients. The gateway also includes a plurality of first message translators. Each first message translator is configured to translate a medical laboratory message that is in a first form, associated with the first translator, into a second form. The gateway also includes an incoming message dispatcher configured to select one of the first message translators, based on source information in received a medical laboratory message and the translation information in the database. The medical laboratory message is translated by the selected first message translator into the second form. The gateway also includes a plurality of second message translators. Each second message translator is configured to generate a medical laboratory message in a third form, associated with the second translator, from the second form. The gateway also includes an outgoing message router configured to select at least one of the second message translators, based on destination information in a received medical laboratory message and the translation information in the database. Each of the selected at least one second message translators generates a message from the second form.

Each of the first message translators may perform a first syntactic translation, a first schematic translation and a first semantic translation, associated with the first translator. Each of the second message translators may perform a second syntactic translation, a second schematic translation and a second semantic translation, associated with the second translator. The second form conforms to a clinical and administrative data message protocol, such as Health Level Seven (HL7), version three.

The gateway may also include an exception handler that is invoked if a first message translator or a second message translator detects an error in a message. Each first message translators may be configured to detect a deviation in a medical laboratory message from a predefined clinical and administrative data message protocol or from a predefined set of diagnostic codes.

The gateway may also include a message store for storing copies of at least portions of at least some of the translated medical laboratory messages. A portal may provide access to the message store.

Yet another embodiment of the present invention provides a method for collecting genetic data about a plurality of patients for subsequent bioinformatic analysis. The method includes receiving medical laboratory report messages generated in response to requests from medical service providers. Each such report may contain genetic data and non-genetic data about a corresponding patient. At least some of the non-genetic data and at least some of the genetic data from the received medical laboratory reports may be stored in a database.

Patient identifying information in the non-genetic data may be anonymized prior to storing the data in the database.

Access may be provided to data stored in the database. Patient identifying information in accessed data may be anonymized. Access may be provided to only data in the database that represents at least a predetermined number of patients.

Storing the data may include selecting ones of the received medical laboratory report messages, based on at least one selection criterion, and storing data from only the selected medical laboratory report messages in the database.

The method may also include automatically detecting statistical correlations between or among data items stored in the database.

The database may be queried to produce a list of tests that may be ordered from a plurality of laboratories. The list may include information about regions examined for DNA variants.

BRIEF DESCRIPTION OF THE DRAWINGS

The invention will be more fully understood by referring to the following Detailed Description of Specific Embodiments in conjunction with the Drawings, of which:

FIG. 4 illustrates a portion of an incoming message in HL7 version 2 form, according to the prior art;

FIG. 5 illustrates a portion of a translated message in canonical form, according to one embodiment of the present invention;

DETAILED DESCRIPTION OF SPECIFIC EMBODIMENTS

In accordance with embodiments of the present invention, methods and apparatus are disclosed for providing a gateway (also referred to as a "VariantWire Gateway" or "VWG") between health care providers ("providers") and laboratories. The gateway enables the laboratories and providers (collectively referred to as "parties" or "clients") to communicate with each other without developing and maintaining an interface for each peer.

The gateway handles medical data messages (which may include genetic and genomic data), such as test requests and test result reports. These messages may include unstructured human-readable reports and structured data representing findings of the reports. Included in the definition of medical data messages are messages containing molecular diagnostic laboratory tests, including genetic, genomic, RNA expression and proteomic analysis, as is frequently used in diagnosing inherited diseases or conditions, identification of individuals at increased risk for inherited diseases or conditions, molecular stratification of disease, molecular characterization or profile of cancer, paternity testing, tissue matching for transplantation and determination of drug efficacy and/or drug metabolism, as well as drug toxicity, collectively "genetic analysis."

THE PRIOR ART

Figure 1:
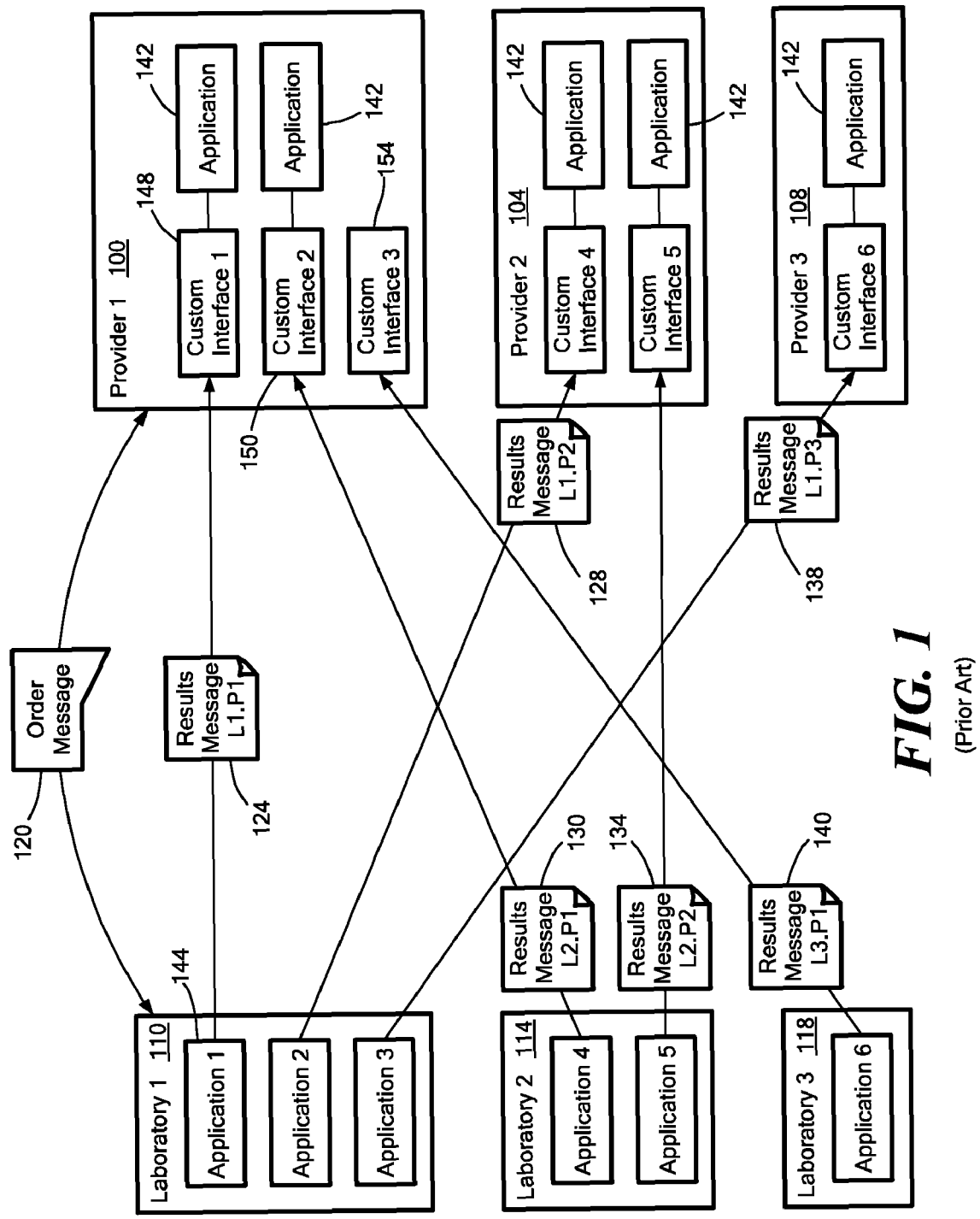
FIG. 1 is a block diagram illustrating exemplary communications between laboratories and providers, according to the prior art.

FIG. 1 is a block diagram illustrating exemplary communications between laboratories and providers, according to the prior art. Each of several providers 100, 104 and 108, sends orders for laboratory tests for patients to individual laboratories 110, 114 and 118. In many cases, these orders are sent via fax, as exemplified by order message 120. Each laboratory sends results messages electronically or via fax, exemplified by messages 124, 128, 130, 134, 138 and 140, to the providers 100-108 that sent the corresponding orders. A laboratory may send one or more messages (such as laboratory test results and various types of acknowledgements, including confirmations and rejections) for each order, as discussed above. In some cases, the providers 100-108 operate applications 142, such as EMRs, which consume data from messages that the providers 100-108 receive.

Each laboratory, and in many cases each application within a given laboratory, uses a unique, often proprietary, message form when generating a message. The form includes laboratory-specific characteristics and/or protocol-specific characteristics, as discussed in more detail below. Exemplary message 124 is generated by an application 144 in laboratory 110, with message characteristics (designated "L1") that may be peculiar to the laboratory 110. In addition, the message 124 is generated according to a protocol P1. Thus, messages from this application 144 have characteristics designated "L1.P1," and such messages require a receiver that is configured specifically for L1.P1-type messages to parse the messages and to extract information from the messages. Other messages 128-140 have designations ("Lx.Py") corresponding to the laboratories that generated the messages and the protocols, according to which the messages were generated.

Each provider that expects to receive messages from a laboratory or a laboratory/application combination may require an individual custom interface to receive and parse messages of the type produced by the sending laboratory or laboratory/application combination and convert the message contents into a form that is usable by the recipient's systems. For example, provider 100 installs custom interfaces 148, 150 and 154 to be able to receive messages from laboratories 110, 114 and 118 and, in some cases, to convert the messages into forms suitable for the provider's applications 142. Similarly, the other providers 104 and 108 install their own custom interfaces, and laboratories may install custom interfaces (not shown) to receive orders electronically from the providers.

However, as the number of providers and/or laboratories increases, the number of custom interfaces greatly increases. As noted, each custom interface is expensive and time-consuming to construct and maintain. The cost to establish even a fraction of the number of interfaces a laboratory or provider would need to electronically communicate with all its peers is beyond the reach of most laboratories and providers.

VariantWire Gateway

The disclosed gateway provides a "hub," through which one or more providers can communicate with one or more laboratories, and vice versa. The gateway reduces or eliminates the need for a custom interface for each peer, from which a provider or laboratory wishes to receive messages. The gateway accepts messages sent by a client in a form preferred by the client. The gateway translates, if necessary, the messages into a canonical form (also referred to as a "common form"). The gateway then generates one or more corresponding messages in forms preferred by intended recipient clients and sends the messages to the recipients.

Figure 2:
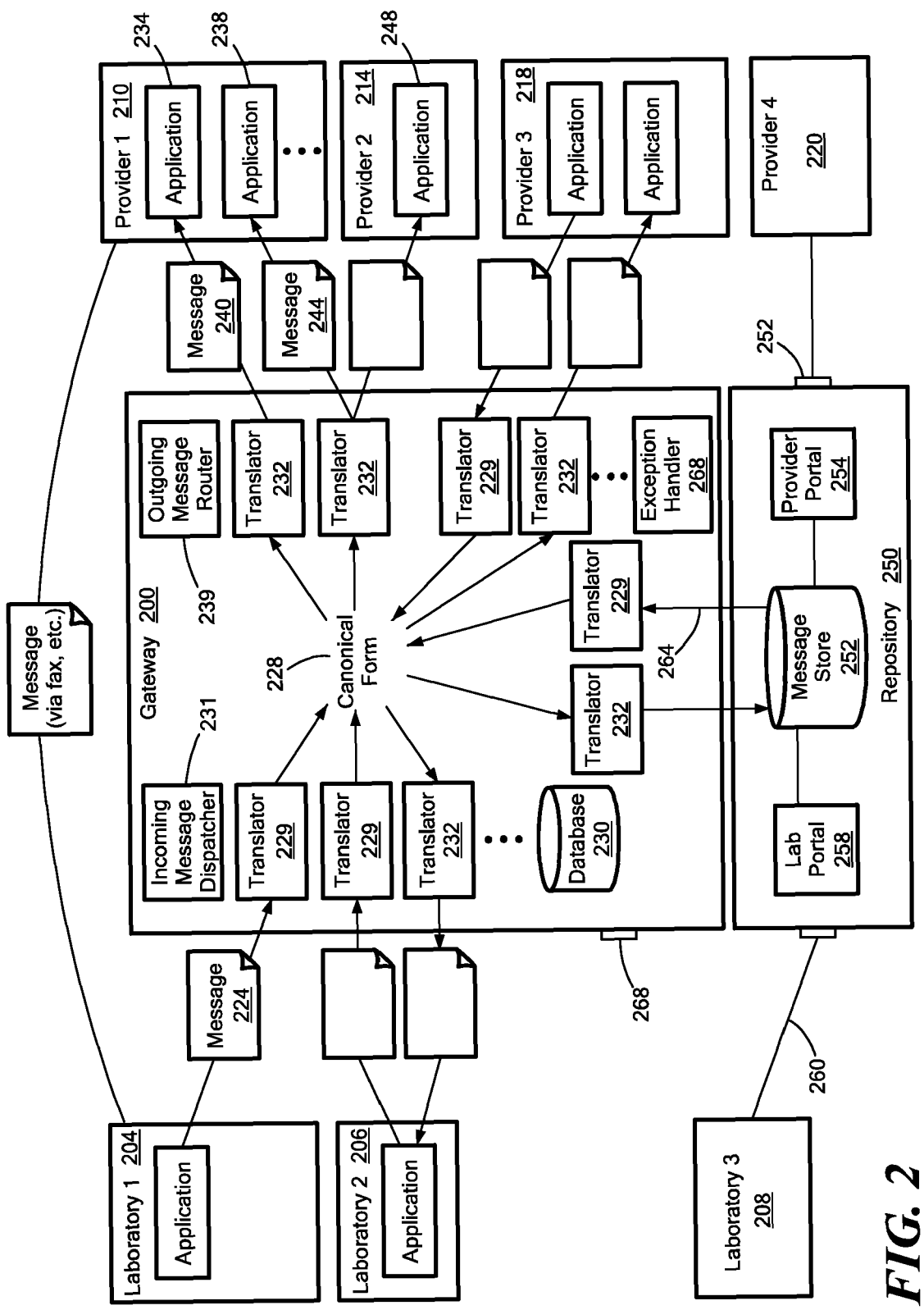
FIG. 2 is a block diagram of a medical message gateway and exemplary communications using the gateway, according to one embodiment of the present invention.

FIG. 2 is a block diagram of an embodiment of the gateway 200 and a number of exemplary clients 204, 208, 210, 214, 218 and 220 communicating with the gateway 200. The gateway 200 is configured to receive messages, such as exemplary message 224. The messages may be medical (including genetic and genomic) laboratory test requests, laboratory test results and various types of acknowledgements, including confirmations and rejections (collectively "medical laboratory test messages"). The gateway 200 is configured to receive each message in a form preferred by the sender of the message and to translate, if necessary, the messages into a canonical form 228. In one embodiment, the canonical form 228 is extensible markup language (XML)-structured HL7, version 3, using Logical Observation Identifiers Names and Codes (LOINC) codes to represent genetic variants. Other suitable standards-based or proprietary canonical forms may be used. Preferably, the canonical form supports hierarchal data.

For each form, in which the gateway 200 is configured to receive messages, the gateway 200 includes an inbound translator 229 to translate received messages into the canonical form 228. The gateway 200 includes a database 230 that contains information about the clients 204-220 that are serviced by the gateway, including information about forms in which the clients send messages and forms in which the clients prefer to receive messages. When the gateway 200 receives a message, an incoming message dispatcher 231 uses information in the message and information in the database 230 to cause an appropriate one of the inbound translators 229 to translate the message into the canonical form 228.

For each received message, the gateway 200 uses information in the received message (or a translated version of the message) to identify an intended recipient client. The gateway 200 then uses the identity of the intended recipient to look up information about the intended recipient in the database 230. Each client may specify one or more receivers (such as applications) that are to receive messages sent to the client, as well as a separate message form for each receiver. For example, Provider 1 may have specified that messages sent to Provider 1 are to be delivered to two applications 234 and 238. Information listing the receivers (in this case, applications 234 and 238) and the forms is stored in the database 230.

For each form, in which the gateway 200 is configured to send messages, the gateway 200 includes an outbound translator 232. An outbound message router 239 uses information in the message and information in the database 230 to cause one or more appropriate outbound translators 232 to generate messages from the canonical form 228. For each receiver 234 and 238 specified in the database, the gateway 200 generates a message 240 and 244 translated from the canonical form message 228, according to the receiver's preferred form(s). The gateway sends the translated messages 240 and 244 to the designated receivers 234 and 238.

The gateway 200 eliminates the need for providers and laboratories to customize their message sending and receiving systems to accommodate each other's message forms. The providers and laboratories may send messages in forms they prefer, and they receive messages in forms they prefer, regardless of their peers' preferences, without the custom interfaces 148-154, etc. (FIG. 1) of the prior art. Thus, the gateway 200 enables any client of the gateway 200 to communicate with any other client of the gateway, without customized software in each client. Furthermore, a new client may be added to the set of clients serviced by the gateway 200 by adding at most one received-message translator (for messages received from the newly added client) and/or at most one sent-message translator (for sending messages to the newly-added client) to the gateway. Once these translator(s) is/are added, the new client can immediately communicate with all the other clients of the gateway 200.

If the new client uses a form that is also used by another client of the gateway 200, an existing translator for the other client may also be used for the new client. For example, if Provider 214 includes an application 248 that accepts messages in the same form as is accepted by another supported application 238, the same outbound translator 232 may be used to translate messages destined to both applications 238 and 248. Of course, translated messages are sent to only the applications/providers to which the messages are addressed. If the new client uses message syntax, schema or semantics that are similar to those of one or more other clients of the gateway 200, new translators may be relatively easily built using the existing translator(s) 229 and/or 232, or a portion thereof, as a model(s).

Centralizing the translation in the gateway reduces or eliminates customization necessary at each client. Furthermore, such centralization makes it much more economical and practical for many providers to communicate with many laboratories than in the prior art (FIG. 1).

Repository and Portals

As noted, some clients are not capable of sending or receiving electronic messages or of sending or receiving all message types. For example, some clients may be limited to sending and/or receiving messages via fax. To facilitate such clients, an embodiment of the gateway maintains a repository 250 that includes a message store 252, in which the gateway 200 stores copies of messages the gateway 200 sent or would have sent to these clients. As shown, the gateway 200 may include translators 229 and 232 for translating messages that are to be stored in the repository 250 or that are generated by the repository 250.

The gateway 200 provides an interface 252, such as a secure web interface or an application service process (ASP), to the gateway 200. The interface 252 may include a provider portal 254 and a laboratory portal 258. Through this interface 252, clients (such as provider 220 and laboratory 208) may access messages or lists of messages in the repository 250. Such access is particularly valuable to clients that are not otherwise capable of receiving messages electronically. Via the interface 252, clients may view messages (such as laboratory reports) and acknowledge receiving the messages or reject the messages. If a client rejects or acknowledges receiving a message (such as a laboratory report), the gateway 200 generates an appropriate rejection or acknowledgement message and sends the message to the client that send the report, including translating the message by an appropriate outgoing translator 232, as described above.

In addition, clients may initiate sending messages to other clients via the interface 252. Thus, if laboratory equipment (such as an application or other equipment in Laboratory 208) is not capable of communicating electronically with the gateway 200, a human or an automated system may enter laboratory analyses (such as by using a browser via the interface 252 to the gateway 200 (as indicated at 260), and the gateway 200 treats the entered information as though it were a message received from the laboratory 208. The repository 250 stores the message in the message store 252 and forwards 264 the message to the gateway 200 for translation and possible forwarding to the destination client. (The translated message may also be sent back to the repository 250, if the intended recipient is incapable of receiving messages electronically.)

The interface 252 may be used on a long-term or interim basis, such as while a client develops an electronic messaging system or an EMR system. Using the interface 252, a client may view the status of a message the client previously sent.

The client may ascertain whether the intended recipient client received the message or whether the message is still stored in the repository 250 without having been read or delivered.

Message Translation

As noted, the gateway 200 includes in-bound translators 229 to translate received messages from the forms in which the messages are received to a canonical form 228. The gateway 200 also includes outbound translators 232 to translate canonical messages to forms in which recipient clients wish to receive messages. Inbound translators 229 are similar in structure and operation to outbound translators 232. The translators are, therefore, described in terms of a source message (i.e., an inbound message or a canonical message) and a destination message (i.e., a canonical message or an outbound message).

Figure 3:
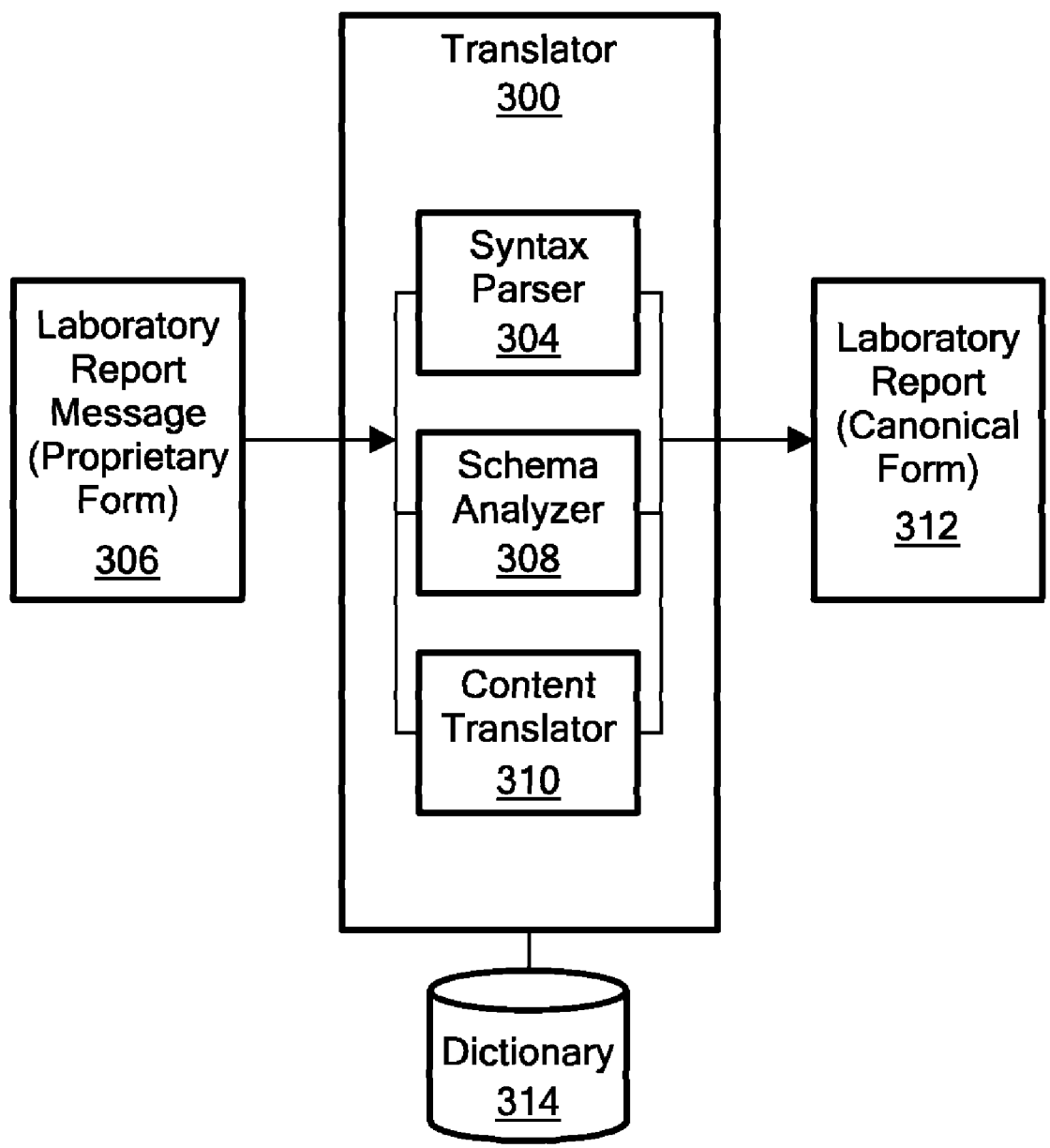
FIG. 3 is a block diagram of a translator of the gateway of FIG. 2.

Depending on the form of a source message, the translation may involve one or more levels of processing. These levels include syntactic (format) translation, schematic (structural) translation and semantic (content or meaning) translation. FIG. 3 is a block diagram of one embodiment of a translator 300. Although FIG. 3 shows an exemplary laboratory message 306 as an input to the translator 300, the description of a translator 300 also applies to translators for messages received from providers and to translators for outbound messages. The translator 300 includes a syntax parser 304, a schema analyzer 308 and a content translator 310, each of which is described below.

Syntactic Translation

At one level of translation, the syntax of a message may be translated. "Syntax" refers to the format (also referred to as grammar) of a message, including character set, record and field layout, key word usage, delimiters and other special characters, etc., without regard to the meanings of values of data items in a message. For example, FIG. 4 illustrates a portion of a source message in HL7 version 2 form. As is well known in the art, an HL7 message contains character data encoded according to the American Standard Code for Information Interchange (ASCII). The character data is divided into segments delimited by carriage return characters.

A typical HL7 message segment begins with a keyword that identifies the segment's type. For example, the first segment 400 begins with a keyword "MSH" 404, which identifies the segment as a message header. The characters 406 following the "MSH" keyword 404 list delimiters that may be used in the message. For example, the first character after the "MSH" keyword 404 (i.e., the pipe character ("|")) is a field separator. The second character (i.e., caret ("^")) is a component separator. The third character (i.e., tilde ("~")) is a repetition separator. The fourth character (i.e., backslash ("\")) is an escape character. The fifth character (i.e., ampersand ("&")) is a subcomponent separator. Other segments in the exemplary message include: patient identification ("PID") 408, patient visit ("PV1") 410, common order ("ORC") 414, observation request ("OBR") 418 and observation ("OBX") 420.

Another exemplary message syntax is the well-known Windows "ini" syntax, which contains ASCII name-value pairs, where each name is separated from its corresponding value by an equal sign ("="), and optional sections delimited by section names enclosed in square brackets ("[" and "]"). Other message syntaxes may include comma-separated value (CSV), SML, resource description framework (RDF), fixed-width definitions (in which each line of a file represents a different record, and each record has a defined order of fields, with each field having a fixed width), SOAP, structured binary and e-mail messages.

Messages need not contain ASCII data. For example, messages may contain data encoded according to another scheme, or they may contain binary data. Messages may have fixed or variable length fields. Fixed-length fields may, but need not, be separated by delimiters.

A message may be formatted according to any agreed upon syntax. Typically, syntax is agreed upon (between a provider or laboratory and an administrator of the gateway) for each application that may send messages to the gateway, and an incoming message syntax translator is associated with each unique incoming syntax. Similarly, syntax is typically agreed upon for each application that may receive messages from the gateway, and an outgoing message syntax translator is associated with each unique outgoing syntax.

The message syntax translator 304 (FIG. 3) parses a source message 306 according to its associated syntax. As noted, some systems may not fully conform to industry message standards. For example, although HL7 specifies fields within a PID (patient identifier) segment, laboratories or providers may insert additional information or deviate from the specified field definitions. The message syntax translator 304 contains logic to parse all possible syntactic structures that may be sent by the sender according to the agreed upon syntax.

If a message syntax translator 304 detects a syntactical error in a message 406, the translator may issue an exception, as described below. Detecting syntactical errors forms part of a message validation function that may be performed by the gateway 200.

Schematic Translation

At a second level of translation, the schematic structure of a message may be translated. A "schema" defines interrelationships between or among portions of a data structure, such as a message. A schema may define relationships between records and fields and provide an underlying organizational pattern or structure of a message. For example, in an HL7 message, an OBX (observation) segment is hierarchically dependent on an OBR (observation request) segment. Several OBX segments may relate to one OBR segment. Fields within a segment may also be structurally (including hierarchically) related to other fields within the same segment. For example, within a PID (patient identifier) segment 408 (FIG. 4), a patient's name may include a last name (ex. "BABB"), a first name (ex. LAWRENCE"), a middle initial (ex. "J") and a generation indicator (such as "Jr.").

The schematic translation need not translate input fields, i.e., fields in a source message, to fields in a destination message on a 1:1 basis. For example, an incoming message may include a patient name (first, middle initial, last, generation, etc.) in one field, possibly with delimiters. However, the canonical message may include separate fields for each of the first name, middle initial, last name, etc. Incoming fields may be decomposed, aggregated and/or translated (or any combination thereof) into canonical message fields. Similarly, canonical message fields may be decomposed, aggregated and/or translated (or any combination) when generating an outgoing message.

A message may be structured according to any agreed upon schema. Typically, a schema is agreed upon (between a provider or laboratory and an administrator of the gateway) for each application that may send messages to the gateway, and an incoming message schematic translator is associated with each unique incoming schema. Similarly, a schema is typically agreed upon for each application that may receive messages from the gateway, and an outgoing message schematic translator is associated with each unique outgoing schema.

As noted, the message syntax translator 304 parses a source message 306 to identify the various portions (records, fields, keywords, etc.) of the source message. The message schematic analyzer 308 processes the identified portions, using information about expected structure and/or relationships among the portions and constraints that bind the portions, i.e., the schema, to construct an equivalent, i.e., translated, destination message 312 that contains the identified incoming message portions organized according to the destination schema. In one embodiment, the canonical message 312 is stored as an XML structure; however, other suitable structures, such as a hierarchy of individual data structures stored in a memory, binary data or character representations may be used.

An incoming message 306 may be only loosely structured or contain unstructured data. In this case, the syntactic parsing and schematic analysis imposes a structure on the data in the message 406. Well-known natural language processing methods may be used to perform the syntactic parsing and schematic analysis.

Among other benefits, restructuring of the incoming message 306 into the canonical message 312 enables the schematic analyzer 308 to identify any structural defects or missing portions in the incoming message. For example, if the canonical schema requires at least one observation for each observation request, but an incoming message 306 contains only an observation request, the schematic analyzer 308 may issue an exception. Similarly, if a required field is overloaded, i.e., two or more fields having the same name appear in a message, the schematic analyzer 308 may issue an exception.

Semantic Translation

At a third level of translation, the semantic meaning of data items in a source message may be translated. Semantics define a vocabulary of data element values that may be used in messages. This vocabulary may be defined by a dictionary, an ontology or other suitable database (collectively referred to herein as a "dictionary").

Semantic translation may involve copying content from one data element in a source message to a semantically identical, although differently named, data element in a destination message. Various providers and laboratories may use different terms for a common concept. For example, one provider may refer to a patient's "age," whereas a laboratory may refer to a patient's "maturity," or one client may refer to "organism," whereas another client may refer to "species." The contents (ex. "*H. sapiens*") of a source data element may be simply copied to a semantically identical, although differently named, data element in a destination message.

Semantic translation may involve reading a data element in a source message and storing a literally different, although semantically equivalent, data element in a destination message. For example, one party may represent race as a text string, such as "Hispanic," whereas another party may encode race using a numeric code, such as 1=White, 2=Native American, 3=Oriental and 4=Hispanic. Similarly, the providers and laboratories may use different data item values, measures, scales, etc. For example, one provider may represent a patient's age in decimal years (such as 15.7), whereas a laboratory may represent a patient's age as an integer number of months (such as 188). Semantic translation may, of course, involve a combination of the processes described above.

A dictionary 314 may be used to translate between terms and values used by one client to canonical terms and values. Optionally or additionally, the dictionary may define a conversion or translation process that is to be performed on the value in the incoming message 306. For example, the conversion process may dictate that the incoming data item value be multiplied by 12 (to convert a number of years into a number of months). The dictionary may contain the address of a conversion or translation routine.

Once the syntax parser 304 and the schematic analyzer 308 construct a canonical translated message 312, the incoming message semantic translator 310 uses the dictionary 314 to translate the data items identified by the syntax parser 304 into canonical representations of the data items. These canonical representations replace the data items in the canonical translated message 312. The semantic translator 310 may use information provided by the syntax parser 304 or the schematic analyzer 308, or information in the translated message 312, about the data item being translated to constrain the dictionary search for the data item or for a translation of the data item. For example, if the data item is known to be a diagnostic code, only dictionary entries that are tagged as being diagnostic codes may be searched.

Alternatively, the syntax parser 304 and schematic analyzer 308 construct an empty message structure 312, and the semantic translator 310 translates the data items identified by the syntax parser 304 and populates the message structure 312 with the canonical, i.e., translated, representations of the data items.

As noted, many diagnostic codes, particularly codes for newly-discovered genetic variations, are not standardized, and sometimes the meanings of existing codes are changed in non-standard ways, leading to semantic differences among laboratories and between laboratories and providers. The semantic translator 310 may translate these codes, such as by using a code translation table (described below). For example, if a laboratory sends information about genetic variants using the HUGO Gene Nomenclature Committee (HGNC) naming convention, an incoming message from this laboratory may contain an OBX segment 428 (FIG. 4) that includes the code "GENE" 430 having an associated value "ACTC1^HGNC" 434. Other laboratories may use other nomenclatures, and a provider may prefer to receive laboratory results expressed in a different nomenclature, such as National Center for Biotechnology Information (NCBI).

The syntax parser 304 detects the caret ("^") 438 component separator between "ACTC1" and "HGNC" in the data value associated with the "GENE" 430 code in the OBX segment 428 to identify "ACTC1" and "HGNC" as distinct components. The schematic analyzer 308 constructs a portion of the translated message 312 to represent a DNA variant, and the semantic translator 310 uses the dictionary 314 to look up "ACTC1" in association with the "HGNC" nomenclature to find a translated value, according to the canonical code values used by the gateway 200. In one embodiment, the canonical code values are NCBI codes.

The previous example also illustrates another point. The value of a data element may be used by the semantic translator 310 to infer structural information about the translated message 312. Thus, the schematic analyzer 308 need not create the entire structure of the translated message 312. For example, the presence of a particular code (ex. "GENE" 430 in an OBX segment or the presence of a gene name in a portion of an incoming message) may be used to infer that one or more elements (ex., "DNA Variant") should be added to the translated message 312, as shown above. Thus, construction of the translated message 312 need not follow a strict onestep-at-a-time process involving first the syntax parser 304, then the schematic analyzer 308 and finally the semantic translator 310. These three components may pass information back and forth between and among them to define the structure of the translated message 312 and/or to construct the message itself.

The semantic translator 310 may issue an exception if a data element value in the incoming message 306 or a not-yet-translated data element value in the translated message 312 is invalid, such as if there is no valid translation of the data element value in question. The gateway 200 may consult a database maintained by a third-party, such as the National Institutes of Health (NIH), to verify a disease name, code or other designation.

FIG. 5 illustrates a portion of a translated message 312 in canonical form. The portion of the message shown in FIG. 5 was translated from portions of the message illustrated in FIG. 4.

As noted, the in-bound translators 229 also translate received diagnostic codes (including genetic variant codes) to common codes. The common codes are also referred to as "standard codes," even though they do not necessarily conform to a generally accepted standard. The common codes may be Logical Observation Identifiers Names and Codes (LOINC) codes, International Classification of Diseases version nine (ICD9) codes, non-standard codes developed for the gateway 200 or a combination thereof.

Some embodiments of the present invention use the extensible stylesheet language (XSL) or the extensible markup language (XML) for message translation or parsing. Other non-procedural and procedural languages (such as Java or C++) may be used to implement translators and other components of the gateway.

Gateway Database

Figure 6:
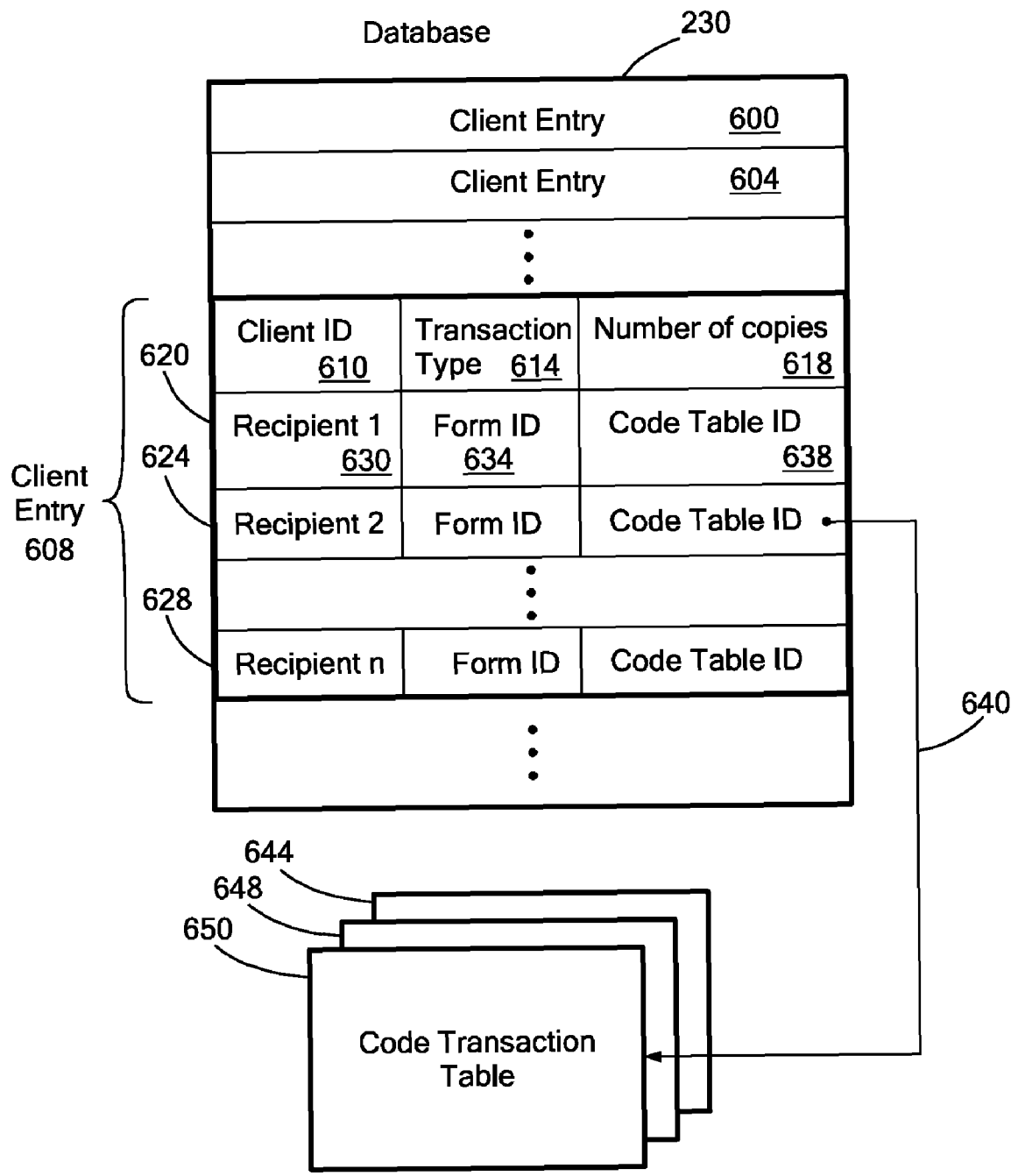
FIG. 6 is a diagram of a database used by the gateway of FIG. 2, according to one embodiment of the present invention.

As noted, the gateway 200 may maintain a database 230 (FIG. 2) that lists clients (laboratories and providers) served by the gateway. The database 230 is used by the gateway 200 to translate incoming messages to the canonical form 228 and to generate outgoing messages from the canonical form 228. FIG. 6 is a diagram of an exemplary implementation of the database 230. Each client is represented by a client entry 600, 604, 608, etc., in the database. Client entry 608 is expanded for clarity.

When the gateway 200 receives a message, the gateway uses information in the message to select a client entry 600-608 that represents the sending client. The gateway 200 uses the selected client entry 600-608 to select an incoming translator 229 to translate the incoming message into the canonical form 228 (FIG. 1).

Each incoming message specifies an intended recipient (client). The gateway 200 uses the identification of the intended recipient client to select the recipient's client entry 600-608 in the database 230. The gateway 200 then uses the recipient's client entry 600-608, and optionally a transaction type of the incoming or translated message, to select one or more outgoing translators 232 to generate one or more outgoing messages for the recipient from the canonical form 228.

As noted, the recipient may receive multiple copies of a message, and each copy may be in a different form. For example, a client may maintain several applications (ex., applications 234 and 238 (FIG. 2)) that participate in the client's workflow, i.e., generating or consuming messages. Each of a client's applications (or a subset of the applications selected based on a transaction type or other selector) receives a copy of each message (or selected messages) sent to the client. For example, a provider may wish to have a copy of each incoming message sent to a central EMR system, as well as to a department or health care professional that or who requested the laboratory test that caused the incoming message to be sent.

Each recipient's client entry 600-608 includes the number 618 of copies of each message (or each type of message) destined to the client that should be sent to the client. For each such copy, the client entry includes a recipient entry, as exemplified by recipient entries 620, 624 and 628. Each recipient entry includes information specifying where each copy should be sent (in a recipient field 630), as well as a form (in a form ID field 634) for the copy and, optionally, information (in a code table ID field 638) about codes used by the receiver for each copy. In one embodiment, the form information is a form identifier, which identifies an outbound translator 232, and the code information is a pointer (exemplified by pointer 640) to one of several code translation tables 644, 648 and 650. The gateway may use the form and code information to translate messages destined to the client (or each application associated with the client) in a way preferred by the client.

Each sender's client entry 600-608 typically contains a "1" in the number of copies field 618, because each inbound message is typically translated into only the canonical form 228. The sender's client entry 600-608 typically contains only one recipient entry, in which the form ID field 634 or the recipient field 630 identifies the appropriate inbound translator 229. The transaction type 614 and recipient 630 fields may be blank.

Messages formatted according to the HL7 protocol typically include a "Sending Facility" field, as well as fields for "Receiving Facility," "Sending Application" and "Receiving Application." Incoming messages formatted according to other standard or non-standard protocols contain equivalent information. In one embodiment, messages sent by clients are addressed, such as in headers of the messages, to the gateway; however, the sending client fills in the Receiving Facility field with an identifier (ID) of the destination facility. Each facility has a unique ID. The sending client fills in the Receiving Application field with an identifier (ID) of an intended recipient application at the receiving facility. In one embodiment, each application has an ID that is unique among all the facilities. In another embodiment, each application has an ID that is unique within the application's facility, but not necessarily among all facilities. In this case, a combination of the facility ID and the application ID uniquely identify the application among all the facilities. The sending client fills in the Sending Facility and Sending Application fields with the sending client's facility ID and application ID, respectively.

The sending client may also include information in the message to indicate a transaction type (also referred to as a "message type"). Some transaction types (for example, "Results Complete" and "Results Confirm Response" messages) have been discussed above. Other transaction types include: "Laboratory Analysis Order," "Order Cancellation," "Order Hold," "Order Status Request," "Order Status Response," "Exception" (such as to indicate a problem with a laboratory analysis order or data) and "Results Nullify." When the gateway 200 receives a message, the gateway parses the message to ascertain the message's type. The message type may be explicitly included in a fixed- or variable-location field of the message, or the message type may be determined by otherwise analyzing the message.

The gateway 200 uses the contents of a received message's Receiving Facility and/or Receiving Application field and, in some cases, the transaction type to look up message processing information in the database 230. For example, the gateway 200 may search the database 230 for a client entry 600, 604, 608, etc. having a client ID field 610 whose contents match the Receiving Facility and/or Receiving Application field of the incoming message and having a transaction type field 614 whose contents match the received message's transaction type. As noted, the located client entry specifies how many copies of the message the gateway 200 is to send to the client, as well as the application(s) to which these messages are to be sent. The gateway may use information in the respective recipient fields 630 to fill in the Receiving Application fields of the messages the gateway 200 sends to the client. Alternatively, the gateway 200 may copy the contents of the Receiving Application field in the incoming message to the outgoing message.

Optionally, the gateway 200 includes a client account management portal 268 (FIG. 2) to allow clients to update their respective information in the database. The management portal may be a secure web interface or other suitable interface. Through the client account management portal, clients may add, change and delete formats, codes and code translations that are to be used for messages destined to the clients.

The messages described herein may be communicated between clients 204-220 (FIG. 2) and the gateway 200 via any suitable electronic communication link (including, but not limited to, the Internet or a private local-area or wide-area network) using any suitable communication protocol (including, but not limited to, TCP, SOAP, SMTP (e-mail), FTP or HTTP). Messages may be in binary, text or other formats.

As noted, many facilities use diagnostic codes, protocols, etc. in non-standard ways. The validation component may be used to enforce a standard, such as by rejecting messages that contain non-standard codes or messages that do not conform to a particular protocol. A gateway with such a validation component may, thus, be used as a centralized authority for enforcing one or more standards.

In some genetic testing, gene sequences are compared to "reference sequences" to identify differences between the tested sequence and the reference sequence. These differences are referred to as "variants," and a nomenclature (included herein in the definition of "codes") is used to describe found variants. The validation component may check message nomenclature that describes variants to ensure the nomenclature is used correctly or to otherwise validate the message nomenclature. In one embodiment, regular expressions are used to check the validity of message nomenclature. Further validation may be performed by validating IDs in the message against external databases or files. As new types of genetic variants are discovered, new nomenclature is defined to identify these new types of variants. The gateway may include a management portal 268 for updating or replacing the databases, files or other data used by the gateway to validate genetic nomenclature.

Figure 7:
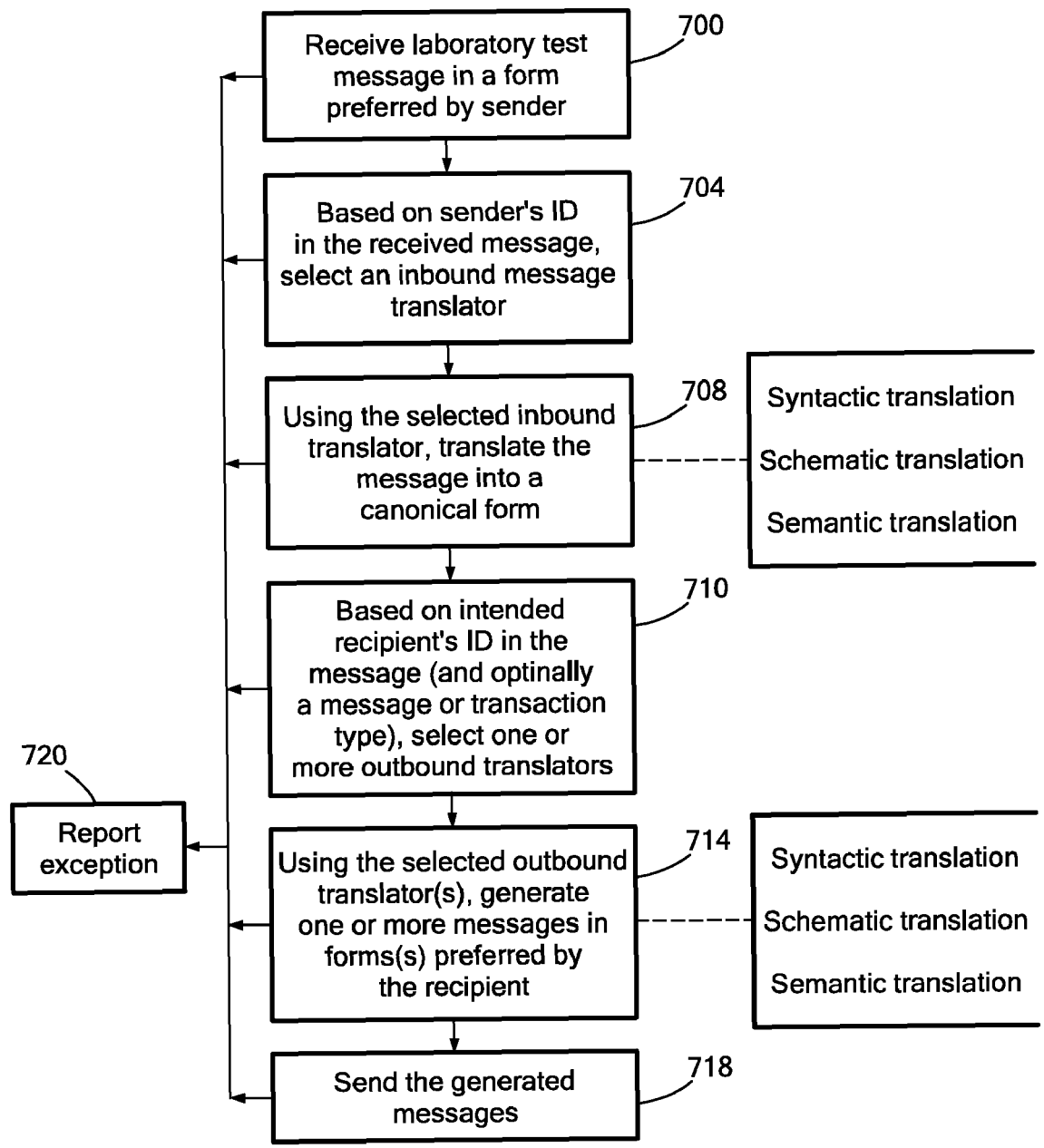
FIG. 7 is a flowchart that describes operation of the gateway of FIG. 2, according to one embodiment of the present invention.

FIG. 7 is a flowchart that describes operation of the gateway 200. At 700, a laboratory test message is received, such as from a provider or from a laboratory, in a form preferred by the sender. At 704, an inbound translator is selected, based on contents of the received message. For example, the sender's identification may be used to locate the sender's client entry 600-608 (FIG. 6) in the database 230, and the client entry may contain an indication, such as in the form ID filed 634, of which inbound translator should be used. At 708, the selected inbound translator translates the received message into the canonical form. This translation may involve syntactic translation, schematic translation and semantic translation.

At 710, based on an intended recipient of the message, one or more outbound translators are selected. For example, a Receiving Facility, Receiving Application and/or transaction type of the message may be used to identify the recipient's client entry in the database 230. Each recipient entry 620-628 in the recipient's client entry may identify an outbound translator. At 714, each of the identified outbound translators generates a message in a specified form, from the canonical form. This translation may involve syntactic translation, schematic translation and semantic translation. At 718, the generated message(s) is (are) sent to the recipient.

Any or all of the processes 700-718 may perform tests to determine if the incoming message is deficient or defective, as discussed above, or to detect other errors, such as a transmission or reception error or an inability to establish a link to an intended recipient and, therefore, an inability to send a generated message. Error checks may include ensuring that required field values are present, validating ranges of values and specialized syntax validation, such as in the case of variant nomenclature. Content validation may include verifying that a name, reference identifier (ID) or other result in a message is listed in a database or file of approved or authorized names, etc. This database may be external to the gateway. For example, the gateway may consult a database maintained by a third-party, such as the National Institutes of Health (NIH), to verify a disease name, code, or other designation. In case an error is detected, an exception report is generated at 720.

If an exception occurs, an exception handler 268 (FIG. 2) may notify the sending client, such as via e-mail, pager or the like. In addition, the exception handler 268 may log exceptions to a log file (not shown). Any component of the gateway 200 may trigger the exception handler 268. Each client may specify one or more addresses and mechanisms, by which the client wishes to be notified of exceptions involving messages sent by or to the client. This information is stored in the database 230 and used by the exception handler 268 to deliver exception messages. In addition, exception messages may be treated like other messages sent to a client, including storing the exception messages in the repository 250. Exception messages identify the sending client, sending application, intended recipient client and application, which gateway component declared the exception, as well as other exception details. For clients that use the repository 250 to access messages, an exception e-mail message, page, etc. may include a hyperlink to an exception message in the repository 250.

Bioinformatic Analysis

Bioinformatic analysis may be preformed on result data flowing through a gateway to discover new clinically relevant correlations between test results in general and patient genotypes in particular or to provide evidence for or against currently suspected correlations. Preferably, the data is secured and patient privacy-protected. No known stream of clinical reports flowing through a hub that interconnects multiple laboratories and multiple providers has been harnessed to yield such genetic data.

When DNA is sequenced, variants are sometimes found. Some of these variants are common, and others are rare or have never been seen before. It is desirable to describe how these variants should be interpreted when reporting clinical test results. However, very little may be known about a variant. Even a small amount of incremental knowledge about variants can be helpful. For example, when analyzing a particular patient's variants, knowing that a particular variant has been seen in some (even a very small number of) other patients before, can be helpful. Knowing that the variant has been seen before with other variants that are known to be pathogenic supports the theory that the seen variant is likely not pathogenic. On the other hand, if the variant has been seen in other patients who have similar symptoms without an alternative genetic cause, this information supports the theory that the seen variant is pathogenic.

Figure 8:
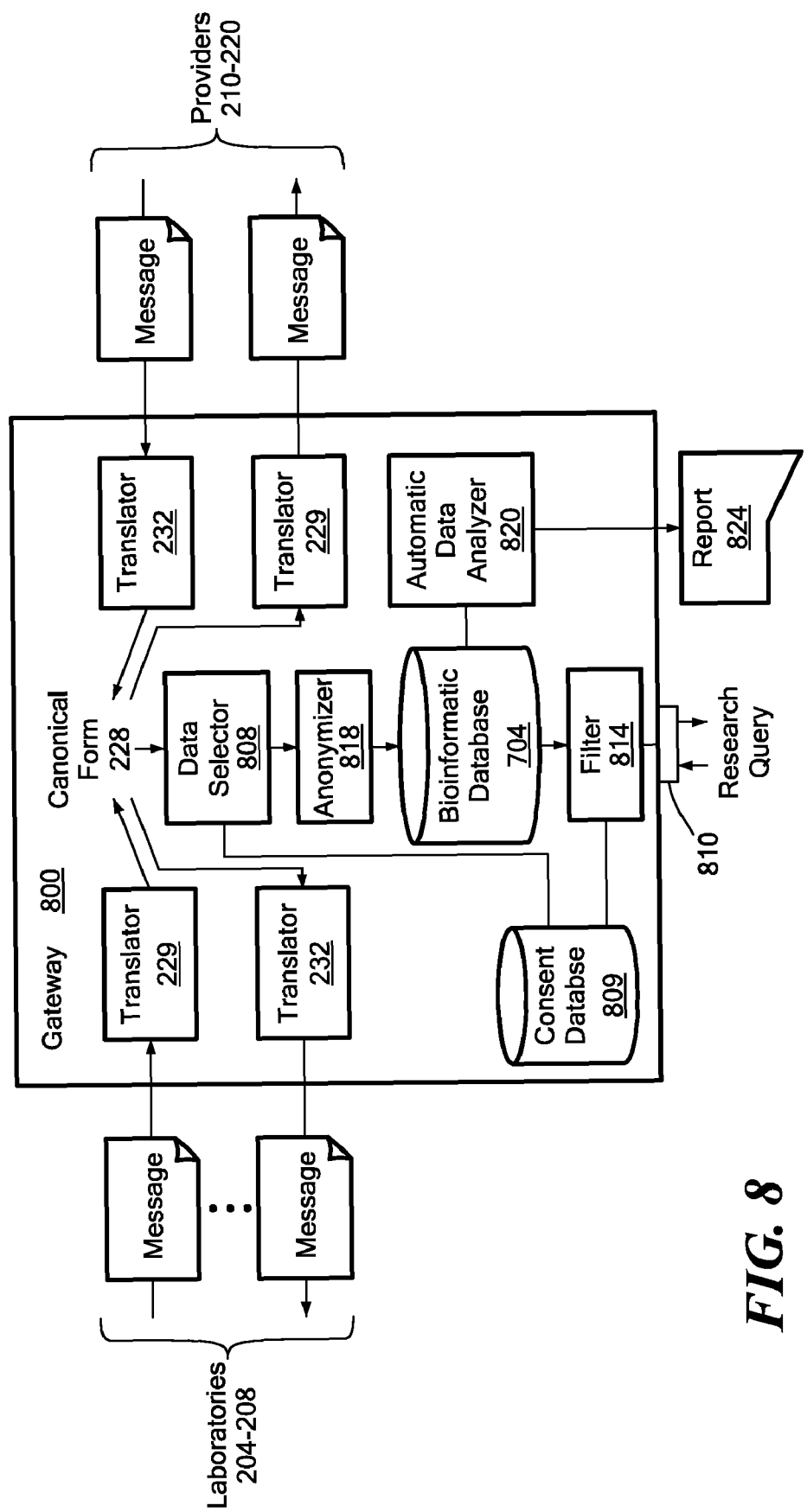
FIG. 8 is a block diagram of a gateway that supports such bioinformatic analysis, according to one embodiment of the present invention.

FIG. 8 is a block diagram of a gateway 800 that supports such bioinformatic analysis. The gateway 800 includes a bioinformatics database 804, which collects and stores copies of result data, and optionally request data, flowing through the gateway 800. Although the bioinformatics database 804 is described in the context of a gateway 800 that translates messages as described above, with respect to gateway 200 (FIG. 2), no such translation is necessary for the bioinformatics database 804. Preferably, messages from multiple laboratories 204-208 flow through the gateway 800 to preferably multiple providers 210-220; however, data from as few as one laboratory, to as few as one provider, may flow through the gateway 800.

Optionally, a data selector 808 selects portions of the data flowing through the gateway 800 for storage in the database 804. Any selection criteria may be used by the selector 808, depending on the types of analysis anticipated. Optionally or alternatively, the data selector 808 may use a consent database 809 to allow only data about patients, or from laboratories, who or that have consented to having their data stored or used for these purposes. The consent database 809 may also be used to implement data collection or query policies formulated by an administrator of the gateway 800.

Typically, results messages from laboratories include information from the requests that ordered the laboratory tests. Thus, information about symptoms is generally included in the results messages, and it may not be necessary to store the request messages in the database 804. However, if the results messages do not include some data that is included in the request messages, the request messages may be stored in the database 804, and data from the results messages may be correlated with the data from the request messages. The correlated data may be consolidated with the request data in the database 804.

An interface 810, such as a web interface or an ASP, provides access by researchers or clinicians, including humans or automated systems, and the like to data in the database 804. The interface 810 may allow the database 804 to be queried using well-know query languages and tools, or portions or all of the database 804 may be exported from the gateway 800 for query and analysis elsewhere.

A filter 814 may be used to limit access to the data in the database 804. The filter 814 may use information stored in the consent database 818. Optionally or alternatively, the filter 814 may implement legal, ethical or other limits on access to the data in the database 804. For example, the filter 814 may disallow access to genetic variant data for an individual patient or group of patients, if the variant is shared by fewer than a predetermined number, such as 1,000, of people. The variant may be identified in the consent database 809 or elsewhere, or the filter 814 may dynamically determine the number of people represented in the database 804 who share the subject variant.

An anonymizer 818 removes, masks or replaces patient-identifying information, such as patient name or patient ID, using well-known techniques, before data is added to the database 804. Optionally, the genetic data may be modified to make it anonymous. Optionally, laboratory-identifying information is also anonymized. Optionally or alternatively, "raw," i.e. non-anonymized data, may be stored in the database 804, and the anonymizer 818 may be connected between the database 804 and interface 810 to anonymize data before it is provided by the interface 810 to an entity external to the gateway 800. As used herein, "patient-identifying information" does not include genetic or genomic data, even though, at least theoretically, a patient may be identified by the genetic or genomic data. Legislation may define patient-identifying information, or a similar term, as including genetic or genomic data for patient protection or other purposes, or legislation may define genetic or genomic data as being inherently identifiable. However, as used herein, the term patient-identifying information does not include such legislative definitions.

Results from analyzing data in the database 804 may form a basis of new drug targets or new molecular diagnostic tests focused on improving patient care. Automatic group or pattern discovery techniques may be used to detect statistically significant correlations between or among portions of laboratory (including genetic or genomic) results, genotypes or variants, patient diseases, reasons for ordering tests or other factors identifiable from laboratory analysis orders or results. For example, an automatic data analyzer 820 may employ known knowledge discovery, data mining or information extraction techniques, such as fuzzy logic, genetic algorithms, group detection algorithms (GDA), k-groups (Kubica, et al., 2003) or algorithms for group discovery on large transactional data (such as XGDA), to discover underlying groups or clusters in the data and produce reports 824. Thus, the gateway 800 enables the discovery of new medical facts. The correlations may be made between pairs of messages, such as between a laboratory order message and a corresponding results message. The large volume of messages passing through the gateway facilitates locating correlations that may not be noticeable in the relatively smaller message volumes handled by individual laboratories or providers.

No known prior art catalog lists laboratory tests and specific structured information describing the exact scope of each test (for example, the exact regions of DNA sequenced by a DNA sequencing test). Thus, ordering a genetic test usually requires manually searching across multiple websites to determine test availability and specificity. In addition, follow-up on "negative" molecular test results, i.e., ones in which no findings were determined to be causal or known to be associated with the condition identified, is challenging.

The gateway 800 solves this problem. Results flowing through the gateway 800 may contain results of laboratory tests performed and associated test definitions. The test definitions may detail the region of a molecule or other genetic and genomic characteristic that was examined during the analysis. These results may be stored in the database 804, and they may be used to provide a test order catalog (i.e., a list of tests that may be ordered from participating laboratories) usable by providers. Thus, the bioinformatics database 704 may be queried to produce a list of tests that may be ordered from a plurality of laboratories, including information about regions examined for DNA variants, such as mutations or Single nucleotide polymorphism (SNP).

When a molecular diagnostic test is found to be "negative," a clinician does not know if the test was negative because: (1) the patient does not have the condition (or risk of developing the condition) or (2) a variant causal to the disease exists in another region of the molecule or another genetic and genomic characteristic not examined by the particular test. To provide a greater level of confidence in the "negative" result, the clinician may compare regions previously examined during testing, regions known to be associated with the condition and regions examined by tests not yet performed on the patient. If there are tests that examine new regions of the molecule or other genetic and genomic characteristics, the clinician may follow up with another test order. In the gateway 800, the automatic data analyzer 820 may be used to recommend additional follow-up testing, on "negative" results, in an automated fashion.

Portions of the gateway 200 or 700 may be implemented using integration software, such as Ensemble, which is available from InterSystems Corporation, Cambridge, Mass. 02142. Portions or all of the gateway 200 or 700 may be implemented using non-procedural or procedural languages, such as Java or C++. All or portions of the gateway 200 or 700 may be implemented by a processor executing instructions stored in a memory.

A medical laboratory report message gateway has been described as including a processor controlled by instructions stored in a memory. The memory may be random access memory (RAM), read-only memory (ROM), flash memory or any other memory, or combination thereof, suitable for storing control software or other instructions and data. Some of the functions performed by the gateways have been described with reference to flowcharts. Those skilled in the art should readily appreciate that functions, operations, decisions, etc. of all or a portion of each block, or a combination of blocks, of the flowcharts may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including computer networks. In addition, while the invention may be embodied in software, the functions necessary to implement the invention may alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Moreover, while the preferred embodiments are described in connection with various illustrative data structures, one skilled in the art will recognize that the system may be embodied using a variety of data structures. Furthermore, disclosed aspects, or portions of these aspects, may be combined in ways not listed above. Accordingly, the invention should not be viewed as limited.

What is claimed is:

1. A medical laboratory report communications gateway computer system for communicating medical laboratory reports between a plurality of clients connected to the communications gateway, the communications gateway computer system comprising:
   a database storing report form data for each of the plurality of clients connected to the communications gateway, the report form data identifying at least one of syntax, schematic, and semantic information describing a report form used by each of the plurality of clients;
   an incoming message dispatcher configured to:
      receive medical laboratory reports from the plurality of clients,
      access the database to determine a report form of each received medical laboratory report using the report form data, and
      select an inbound translation to perform on each received medical laboratory report based upon the report form of each received medical laboratory report;
   an inbound message translator configured to:
      receive a medical laboratory report from the incoming message dispatcher, and
      use the report form data stored in the database to perform an inbound translation on the medical laboratory report to transform the medical laboratory report to a canonical form;
   an outgoing message router configured to:
      receive the medical laboratory report in the canonical form,
      identify a destination client for the medical laboratory report, and
      use the report form data in the database to determine an outbound message form based on the destination client, and
      select an outbound translation to perform on the medical laboratory report in the canonical form; and
   an outbound message translator configured to:
      receive the medical laboratory report in the canonical form, and
      perform the selected outbound translation on the medical laboratory report in the canonical form to transform the medical laboratory report in the canonical form into a form useable by the destination client, and
      transmit the translated medical laboratory report to the destination client.

2. The communications gateway computer system as recited in claim 1 wherein a medical laboratory report includes data related to at least one of medical test requests, medical test results, and molecular diagnostic laboratory tests including information acquired from at least one of genetic, genomic, RNA expression, and proteomic analysis.

3. The communications gateway computer system as recited in claim 1 wherein the clients connected to the communications gateway include at least one of a health care provider, a medical laboratory, and applications and laboratory equipment located within at least one of a healthcare provider and a medical laboratory.

4. The communications gateway computer system as recited in claim 1 further comprising a repository including:
   a message store configured to store translated medical reports; and
   an interface connected to the message store and configured to provide clients connected to the communications gateway with controlled access to the stored medical reports.

5. The communications gateway computer system as recited in claim 4 wherein the interface is further configured to allow a client connected to the communications gateway to:
   view and acknowledge receipt of medical laboratory reports;
   initiate sending messages to other clients connected to the communications gateway; and
   view a status of previously sent medical laboratory reports.

6. The communications gateway computer system as recited in claim 1 wherein the inbound and outbound message translators include at least one of a syntax parser configured to perform syntactical translation, a schema analyzer configured to perform schematic translation, and a content translator configured to perform semantic translation.

7. The communications gateway computer system as recited in claim 6 wherein syntactical translation includes formatting a medical laboratory report to a selected syntax, schematic translation includes changing an underlying organizational structure of the medical laboratory report, and semantic translation includes changing a semantic meaning of data items in the medical laboratory report.

8. The communications gateway computer system as recited in claim 1 further comprising a plurality of inbound message translators, each configured to perform a different inbound translation, and wherein selecting and performing the inbound translation includes routing the medical laboratory report from the incoming message dispatcher to a selected one of the plurality of inbound message translators.

9. The communications gateway computer system as recited in claim 8 further comprising a plurality of outbound message translators, each configured to perform a different outbound translation, and wherein selecting and performing the outbound translation includes routing the medical laboratory report having the canonical form from the outgoing message router to a selected one of the plurality of outbound message translators.

10. The communications gateway computer system as recited in claim 9 wherein connecting a new client to the communications gateway includes adding at least one of an inbound message translator and outbound message translator to perform translations associated with the client.

11. The communications gateway computer system as recited in claim 1 wherein multiple copies of a given medical laboratory report, each having a different form, are transmitted to a single client.

12. The communications gateway computer system as recited in claim 1 further comprising:
   a bioinformatics database configured to collect and store copies of medical laboratory reports passing through the communications gateway;
   an automatic data analyzer configured to analyze medical laboratory reports stored in the bioinformatics database and identify underlying groups and clusters of information in data contained in the analyzed reports; and
   an interface configured to provide controlled bioinformatics database access to clients and allow the bioinformatics database to be queried.

13. The communications gateway computer system as recited in claim 1 further comprising:
   an anonymizer configured to mask patient-identifying information in medical laboratory reports stored to the bioinformatics database; and
   a consent database configured to limit the storage of medical laboratory reports to the bioinformatics database to consented medical laboratory reports.

14. The communications gateway computer system as recited in claim 1 wherein the bioinformatics database can be queried by clients connected to the communications gateway to produce a list of medical tests performed by clients connected to the bioinformatics database.

15. The communications gateway computer system as recited in claim 1 further comprising an exception handler configured to log and report identified deficient medical laboratory reports and defective medical laboratory reports.

* * * * *